(12) United States Patent
Kostrzewa et al.

(10) Patent No.: US 10,043,647 B2
(45) Date of Patent: Aug. 7, 2018

(54) DEPOSITION AID FOR THE MANUAL DEPOSITION OF MASS SPECTROMETRIC SAMPLES

(71) Applicants: Bruker Daltonik GmbH, Bremen (DE); Christiane Boogen, Cologne (DE)

(72) Inventors: Markus Kostrzewa, Lilenthal (DE); Ulrich Weller, Cologne (DE)

( * ) Notice: Subject to any disclaimer, the term of this patent is extended or adjusted under 35 U.S.C. 154(b) by 1212 days.

(21) Appl. No.: 13/904,199

(22) Filed: May 29, 2013

(65) Prior Publication Data

US 2015/0357172 A1 Dec. 10, 2015

Related U.S. Application Data

(63) Continuation of application No. PCT/EP2011/070839, filed on Nov. 23, 2011.

(30) Foreign Application Priority Data

Nov. 30, 2010 (DE) .................... 10 2010 052 976

(51) Int. Cl.
*H01J 49/04* (2006.01)
*H01J 49/16* (2006.01)
*B01L 9/00* (2006.01)
*B01L 3/00* (2006.01)
*B01L 99/00* (2010.01)
*G01N 1/28* (2006.01)
*G01N 1/04* (2006.01)

(52) U.S. Cl.
CPC .......... *H01J 49/0413* (2013.01); *B01L 3/545* (2013.01); *B01L 9/523* (2013.01); *B01L 99/00* (2013.01); *G01N 1/28* (2013.01); *H01J 49/0418* (2013.01); *B01L 2300/0645* (2013.01); *B01L 2300/0829* (2013.01); *G01N 2001/045* (2013.01)

(58) Field of Classification Search
None
See application file for complete search history.

(56) References Cited

U.S. PATENT DOCUMENTS

| 4,692,609 | A | 9/1987 | Pettersson | |
| 6,670,609 | B2* | 12/2003 | Franzen | H01J 49/0418 250/288 |
| 2002/0055179 | A1* | 5/2002 | Busey | B01L 3/5085 436/172 |
| 2004/0183009 | A1* | 9/2004 | Reilly | H01J 49/164 250/288 |

(Continued)

FOREIGN PATENT DOCUMENTS

| DE | 8814762.2 B1 | 1/1989 |
| DE | 202005017946 B2 | 1/2006 |

(Continued)

*Primary Examiner* — Binu Thomas
(74) *Attorney, Agent, or Firm* — Benoît & Côté Inc.

(57) ABSTRACT

The invention concerns the reduction of the risk of an incorrect assignment of samples to sample sites during the manual deposition of samples for ionization by laser desorption (for example MALDI or LDCI). The invention offers a method wherein a sample support with several sample sites is provided, at least one sample site is selected, and the selected sample site is highlighted, at least in contrast to neighboring not selected sample sites, in a way which the human eye can perceive.

14 Claims, 5 Drawing Sheets

(56) References Cited

U.S. PATENT DOCUMENTS

| | | | |
|---|---|---|---|
| 2005/0036036 A1* | 2/2005 | Stevenson | G08B 13/19689 348/211.99 |
| 2005/0259256 A1 | 11/2005 | Anselmetti et al. | |
| 2006/0278824 A1* | 12/2006 | Truche | G03B 15/07 250/288 |
| 2007/0072168 A1* | 3/2007 | Ryle | B01L 3/545 435/4 |
| 2010/0321696 A1* | 12/2010 | Malik | G01N 21/645 356/432 |
| 2013/0302847 A1* | 11/2013 | Mix | H01J 49/0413 435/29 |
| 2013/0323406 A1* | 12/2013 | Schmid | B01L 9/50 427/8 |

FOREIGN PATENT DOCUMENTS

| | | |
|---|---|---|
| DE | 202007018535 B2 | 12/2008 |
| DE | 102008010267 A1 | 8/2009 |
| WO | 9839475 A2 | 9/1998 |
| WO | 2004083811 A2 | 9/2004 |

* cited by examiner

DEPOSITION AID FOR THE MANUAL DEPOSITION OF MASS SPECTROMETRIC SAMPLES

BACKGROUND OF THE INVENTION

Field of the Invention

The invention concerns methods helping the manual deposition of samples, preferably of biological material, on a mass spectrometric sample support for ionization by laser desorption, preferably by matrix assisted laser desorption, and corresponding deposition aids.

Description of the Related Art

The rapid, error-free identification of microorganisms plays a prominent role in the analysis of food, in the monitoring and control of biotechnological processes, in the detection of biological weapons and particularly in clinical microbiology. Microorganisms, which are also called germs or microbes, are usually microscopically small living organisms which include bacteria, fungi (e.g. yeasts), microscopic algae, protozoa—for example plasmodia, which cause malaria—and in some sense also viruses.

The identification of bacteria by mass spectrometric detection methods has been described in detail in a scientific review article by van Baar, for example (FEMS Microbiology Reviews, 24, 2000, 193-219: "Characterization of bacteria by matrix-assisted laser desorption/ionization and electrospray mass spectrometry"). In most cases the identification is achieved by means of a similarity analysis between a mass spectrum of the sample under investigation and reference spectra of known microorganisms. The similarity analysis involves assigning each reference spectrum a similarity indicator which is a measure of the agreement between the relevant reference spectrum and the mass spectrum of the sample (see for example Jarman et al., Analytical Chemistry, 72[6], 1217-1223, 2000: "An algorithm for automated bacterial identification using matrix-assisted laser desorption/ionization mass spectrometry").

In recent years, this simple and low-cost method for the mass-spectrometric identification of microorganisms based on MALDI time-of-flight mass spectra (MALDI=matrix assisted laser desorption and ionization) has become established for routine work in clinical microbiology.

The starting point for the mass spectrometric identification is a small quantity of microorganisms, which are usually cultured in a culture dish, such as a Petri dish with a nutrient medium (agar plate), for some hours—usually overnight culture—up to a few days. The aim is that the colonies grown in the agar plate each contain only species of one single microorganism, i.e. they form a pure culture. The usual method of sample preparation is to manually take up biological material of a single colony on an agar plate with an inoculation swab, a type of toothpick, for example, and transfer it to a sample site on a MALDI sample support. Conventional MALDI sample supports have between 6 and 1536, in particular 48 to 384 sample sites. If the quantity of sample transferred with the inoculation swab can just be seen with the naked eye, it is already dosed a little high for a mass spectrometric investigation. One million microbes in the sample makes the sample just visible; the optimum number for excellent mass spectra amounts to some 100,000 microbes.

The transferred cells are usually destroyed by the addition of an organic solvent in which a matrix substance is dissolved. This releases molecular cell components from the inside of the cell, in particular soluble proteins which are present in high concentration. The organic solvent evaporates during air-drying and the matrix substance crystallizes. The molecular cell components released in this process are incorporated into the polycrystalline matrix layer. New inoculation swabs are used for the preparation of further sample sites on the MALDI sample support in order to prevent cross-contamination.

After the preparation, the MALDI sample support is introduced into a MALDI time-of-flight mass spectrometer, where the sample sites are bombarded with laser pulses. In this way, the molecular cell components embedded in the matrix layer are desorbed and ionized together with the matrix substance. The ions are accelerated in an electric field and impact on a detector after mass-dependent times of flight. The times of flight of the ions measured with the detector are converted into mass-to-charge ratios m/z with the aid of known mass calibration functions. The measured signals can often be traced back to proteins which are specific for the species of the microorganism and sometimes even for the strain. The mass spectrum can thus be interpreted as a molecular fingerprint and can be used for microbial identification in particular.

The publication DE 10 2004 020 885 A1 is concerned with the preparation of samples of microbial origin on MALDI sample supports with the objective of automating the transfer of biological materials from agar plates to sample sites on MALDI sample supports. To this end, agar plates are transported via a conveyor belt to a robot and set down on a 3D stage. An image processing system recognizes separated colonies on the agar plate and positions a sampling rod accordingly. An individual sampling rod is used for one single transfer only and replaced afterwards. Biological materials are taken up by the sampling rod being released from a holder and dropping from a height of a few millimeters onto the colony. The contact with the colony thus achieved is intended to ensure that only biological material adheres to the sampling rod, and no agar is transferred onto the MALDI sample support. If too much agar is transferred onto the MALDI sample support, the quality of the mass spectrometric identification is reduced because agar suppresses the signals of the characteristic protein ions. A high-precision sensor system to control the contact is not provided. The sampling rod does, however, vibrate, and it can be wetted with water before the sampling in order that a sufficient quantity of biological material from a colony adheres to the sampling rod and can be transferred onto a sample site of a MALDI sample support.

In a semi-automatic sampling system, a single colony from which biological material is to be transferred onto a MALDI sample support is selected by a user selecting and marking the single colonies on an image of the agar plate taken by a camera, for example, before the automatic transfer.

The advantage of an automatic and semi-automatic transfer from an agar plate onto a MALDI sample support consists in the agar plate and the sampling location on the agar plate being uniquely assigned to the sample sites of a MALDI sample support, and samples of microbial origin from different colonies being transferred to one single sample site, thus preventing any mix-up. If, in addition, an image of the sampling on the agar plate is acquired and stored, even an individual colony can be uniquely assigned to a sample site. The agar plates and the MALDI sample supports are nowadays usually provided with corresponding codings, such as barcodes or RFID chips (RFID=radio frequency identification). The journey of a sample from its arrival in the laboratory—or even from it being taken at the doctor's office—through to the acquisition and evaluation of the mass spectra can therefore be traced back in an unbroken chain.

With manual transfer, on the other hand, transfer mistakes can easily happen, with the result that several samples of microbial origin are transferred onto one sample site as a result of a mistake by the laboratory staff, or the assignment of samples on the MALDI sample support is incorrectly recorded in a laboratory information and management system. In these cases the identification of the microorganisms is also erroneous, of course. The automation of the sample transfer has gained very little acceptance so far, however, because the mass spectra of manually prepared samples have a higher quality throughout. There is therefore a need to improve the methods of manual preparation.

The utility model DE 20 2007 018 535 U1 describes a pipetting aid for transparent microtiter plates, which are put into a base plate with the aid of an adapter. The base plate contains sources of light, which are each assigned to an opening in the adapter and a cavity of the transparent microtiter plate. A switching or control unit activates the light sources independently of each other, and the light passing through the adapter and the transparent microtiter plate indicates where a sample liquid is to be pipetted. In contrast to the microtiter plates, sample supports for ionization with matrix assisted laser desorption are generally opaque. This is usually a result of their electrical conductivity, which serves to prevent static charges on the sample support, which can form during the laser desorption. Electrical conductivity is fundamentally undesirable for microtiter plates because the cavities—in contrast to the flat sample sites on the MALDI sample supports, which are, to a large extent, designed flush with the rest of the surface—provide a larger interaction area with the pipetted sample liquid. This enlarged interaction area can—if the plate is conductive and the samples are liquid—promote undesirable boundary layer processes, for example the deposition of charge carriers which are dissolved in the liquid, such as salts, or chemical boundary layer reactions.

It is relatively easy for a lab technician who has transferred sample liquid onto a microtiter plate to recognize which cavities contain the sample liquid and which do not. This particularly results from the fact that, for manual pipetting, at least one microliter of sample liquid has to be transferred because it is not usually possible to precisely measure a smaller amount with the pipettes used. The quantity of one microliter is sufficiently large that a person can recognize it with certainty with the naked eye, which is also guided by the cavities themselves to some degree.

When a flat MALDI sample support plate is spotted with microorganisms, it is hardly possible to recognize correctly dosed samples with the eye. In laboratory practice, one occasionally resorts to picking up the sample support in the hand after applying a sample and holding it against the light to make out a sample on the sample site. Only if the matrix substance with solvent is applied to a sample site immediately after applying the analyte substance of interest, such as biological materials from a cultured microbe colony, can the lab technician clearly recognize the distribution of the samples on the sample support at a glance and without much effort because the light reflection and scattering properties of the liquid spot—or the matrix crystal layer produced on the sample site after this liquid has evaporated—differ from those of the rest of the sample support surface. However, this procedure of applying the matrix solution immediately makes the spotting sequence less flexible, which a lab technician usually finds unhelpful. In addition, confusion can occur if, for example, the technician is distracted during the spotting sequence and forgets to apply matrix substance with solvent onto a sample site previously spotted with an analyte substance.

As a result of these considerations it would be expedient to, in particular, reduce the risk of an incorrect assignment of the samples to the sample sites during the manual depositing and preparation of samples for ionization with matrix assisted laser desorption.

SUMMARY OF THE INVENTION

It is suggested to provide a sample support with several sample sites for the manual depositing and preparation of samples for ionization with matrix assisted laser desorption, selecting at least one sample site and highlighting the selected sample site in a way which can be perceived by the human eye, at least with respect to neighboring, not selected sample sites. The highlighting may be performed by mechanical pointing devices or by beams of light which preferably originate from light sources or light guiding systems substantially located at the upper side of the sample support or, in other words, at the side of the sample support facing an operator.

A technician manually carrying out the preparation of samples on a sample support is assisted in depositing a sample taken from a nutrient medium—agar plate, bouillon or blood culture, for example—at the correct sample site by the visually recognizable highlighting. The risk of deposition errors, which essentially occur because the small quantity of sample material transferred is usually hardly perceptible to the eye, can thus be reduced.

The highlighting here shall particularly be reversible, i.e. it can be activated and deactivated. The aim is to facilitate the work of a technician, in particular by the selection and the highlighting being carried out (semi-) automatically with electronically assisted means. The procedural effort involved can be minimized if the highlighting of the selected sample site is limited to contrast with the immediately adjacent ones which have not been selected. The highlighting effect can, however, be enhanced by increasing the number of not selected sample sites, in the extreme case such that the selected sample site is highlighted with respect to all other, not selected sample sites.

In the following, MALDI is given as the preferred type of ionization, where ions are created during desorption brought about by a laser. However, it is obvious that, in the present invention, only the laser desorption for transferring the analyte substances—i.e. proteins or protein chains—into the gaseous phase is important. The type of ionization can be selected as required to suit the application. The laser desorption can be followed by chemical ionization (LDCI) of the desorbed molecules, for example, but other types of ionization can also be used. The term ionization with matrix assisted laser desorption must be understood in a correspondingly broad sense.

The sample site can be selected on the basis that there is no sample deposited. The method provides certain flexibility in the different stages of a depositing sequence. It is also possible to make a geometric selection, for example by specifying that only every $n^{th}$—e.g. every second—sample site is to be spotted. This may be sensible if the danger of a cross-contamination by outgassing of a sample and transfer of the outgassed sample particles in the gas phase onto a different sample site is increased by the layered sample sites being close together. In one version of the method, the selection can be carried out by an electronically assisted technical control system, where all unspotted sample sites are spotted, for example, or alternatively by a user of the method.

The selected sample site can be highlighted mechanically, with the aid of a light effect, or a combination of both. The key criterion is that the highlighting of the sample site enables the user of the method to recognize on which sample site he is to deposit a sample. This can be carried out mechanically, for example, by means of an adjustable pointer on the surface of the sample support whose tip can be pointed toward the sample site selected. Furthermore, it is possible to illuminate the selected sample site from above. Generating an enhanced color and/or brightness contrast in comparison to the surrounding, not selected sample sites enables the selected sample site to be particularly clearly marked. Additionally, or alternatively, an opening of a mask can be positioned on the surface of the sample support at the position of the sample site, preferably covering the immediately adjacent sample sites thereby rendering them inaccessible.

In one embodiment, the sample support can be manufactured at least partially from a plastic which responds to voltages. The sample support can then be separated into several areas, each containing sample sites, which can be separately supplied with a voltage. Under the influence of the voltage, the corresponding area changes its light reflection properties, from partially transparent to opaque or vice versa, for example. In this way a brightness contrast can be generated without the need for a separate light source. Rather, in this example, the ever present room light (in the laboratory) which shines onto the surface of the sample support from above can be used to generate a light effect by changing the characteristics of the surface reflecting the light.

In various embodiments the selected sample site is illuminated from above by a suitable light source, such as a spotlight or the like. Preferably, the light source is configured such that the angle of light incident on the selected sample site relative to the surface of the sample support is rather small, such as smaller than 30° or even smaller than 20° or even smaller than 10° or even smaller than 5°. In this manner, shadowing of the highlighted sample site brought about when a tip of a pipette or an inoculation swab approaches the highlighted sample site and crosses the light beam can be delayed up to a short time before the deposition so that the risk of a user being confused by the shadowing and thereby losing focus of the right sample site can be reduced.

In a further development of the method, several sample sites can be selected and the highlighting can be carried out repeatedly in a spotting process, where a different sample site is highlighted with every repeat. This development is particularly suitable for the sequential processing of different samples which originate from different colonies on a culture plate and are to be applied to a sample support. With such a sequential processing, it is preferable to use a monitoring and control system which assists the user of the method in selecting the samples to be transferred.

Another embodiment comprises a method for the manual deposition of a sample on a sample support for ionization with matrix assisted laser desorption in which the sample and the sample sites are each given identification tags, a sample site is selected and highlighted in accordance with a method described above, the sample is applied to the selected sample site, and the identification tags are assigned to each other and stored. In this way, after the spotting of the sample support, it is possible to trace back and check which samples with which origin have been transferred onto a specific sample site. This allows a subsequent process control and can show up errors, for example, if a sample of particular origin was deposited on two sample sites, although for each sample of the origin in question only one sample site was planned. The assignment and storage can be carried out jointly in a combined method step, or separately. For example, the assignment can be carried out before the actual spotting process, and the storage after the conclusion of the spotting process. A specific temporal sequence of the assignment and the storage during the method is not mandatory in principle. It is preferable, however, to assign and store the identification tags after the spotting process, because in this way an incorrect assignment or incorrect spotting can be more easily identified.

As samples to be deposited, samples of microbial origin are particularly suitable, even in an untreated form, such as microorganisms as they were cultured in a nutrient medium.

The identification tag of the sample can be derived from the labeling of the sample vessel—a Petri dish, for example—from which the sample originates. This gives a high degree of traceability for the sample. It is also possible to generate or supplement an identification tag by using a camera to take a picture of the sample source, in particular the flat nutrient medium in a Petri dish, and determining the coordinates of the sample origin in the image by means of image processing and assigning them to the sample. As an addition or alternative to an optical image of the flat nutrient medium, the sample origin can be identified by measuring the capacitance change on the flat nutrient medium before the sampling compared with after the sampling.

In one version, the sample origin data and/or identification tags can be transmitted to the sample preparation instrumentation via telecommunications equipment in order to be stored there together with the spotting coordinates and/or the identification tags of the sample support or the sample site, after completion of the spotting of a sample site on a sample support. It is then possible to undertake a particularly detailed sample trace back.

A further embodiment concerns a deposition aid for the manual deposition of samples on a sample support for ionization with matrix assisted laser desorption. The deposition aid has a holder for a sample support with several sample sites which is adapted to standardized sample supports for ionization with matrix assisted laser desorption. There is furthermore a device that, when a sample support is inserted in the holder, is located substantially at the upper side of the sample support, and which highlights at least one selected sample site at the front of the sample support, at least with respect to neighboring not selected sample sites in a way which a person can see. Furthermore, the deposition aid contains a control system, which selects at least one sample site and controls the device in such a way that the selected site is highlighted.

The holder is adapted, preferably in terms of its geometry, to standardized sample supports for ionization with matrix assisted laser desorption. This adaptation can also be carried out using adapter pieces which are inserted into a holder. Sample supports of different configurations or dimensions can thus be fitted into the holder. This makes it possible to arrange the sample supports in the holder so as to be flush and/or aligned. The standardization of the sample supports is defined in particular via the geometric dimensions, such as height, length, width or area, the number of sample sites or their (matrix) arrangement, particularly in rows and columns. It must be borne in mind that sample supports which are used in laser desorption methods must have a surface which is as plane as possible in order for the boundary conditions for the electric fields created in the space in front of the sample support to be as homogeneous as possible. This facilitates the control of the region in the phase space (generated from space and momentum coordinates), which is occupied by the ions of interest created in the laser desorption process. Cavities, recessed into microtiter plates, are not suitable for this.

The device can operate in such a way that, at the sample site selected, it generates a contrast in brightness and/or color at least to the neighboring not selected sample sites. One possibility is to provide a light source whose light is focused and directed as a light beam from above onto a sample site.

The deposition aid can alternately be equipped with an adjustable indicator. In a simple case, the indicator can be a pointer located above the sample sites, which is moved relative to the sample support. The device can also be provided additionally or alternatively with an acceptance element which allows manual access to a selected sample site and prevents access at least to neighboring not selected sample sites. In one version of the embodiment, the acceptance element consists of a perforated plate and is preferably designed as a type of mask to expose the sample site selected and cover at least neighboring not selected sample sites.

The deposition aid can, in particular, be equipped with a movement device which communicates with the control system and is controlled by it in such a way that it moves the holder for the sample support and the device relative to each other. It does not matter whether the holder and the sample support which is inserted into it during a spotting process or—in a kinematic reversal—the device is adjustable. It is also possible to design both the holder and the device to be adjustable. The movement device ensures that every sample site can be reached and highlighted with the highlighting measures.

The control system can be provided with an interface for data input or output. This is particularly useful if a user wants to enter or read in a spotting plan of a sample support to be processed into the control system. The interface can also be used with manual input, for example, for confirmation of a spotting process which has been carried out. In this way a sequence of spotting processes can be carried out reliably. As an extension, the interface can also have a telecommunication function for receiving sample origin data and/or corresponding identification tags, for example, which can then be stored with the spotting data and/or corresponding identification tags of the spotted sample sites in order to be able to assign them. The telecommunication function can also incorporate the transmission of corresponding data. The telecommunication function can be established with known telecommunication means such as wireless, Bluetooth, infrared or other interface.

The control system can, in addition, have a memory for the assignment and acquisition of identification tags of samples and sample sites. The assignments made are securely stored there and can be queried as often as desired for a subsequent evaluation or check.

In one embodiment, the deposition aid can be stationary. It is then preferably located in an arrangement of a culture plate support, on which Petri dishes for the sampling can be arranged, for example, and a mass spectrometric sample feeding station with a laser desorption device in such a way that the sample can be transferred from the culture plate support to the deposition aid, and from there to the feeding station, in as time-saving a way as possible.

In a further version, the deposition aid can be designed to be portable. As a portable handheld unit, for example, the deposition aid can be carried by a technician like a painter's palette in or on the hand. In this case, the deposition aid preferably has a holding device such as a grip, blind holes suitable for a human hand, or a holding strap, with which it can be fastened to the user's arm. Portability can also be achieved by the deposition aid being designed like a vendor's tray, for example with at least one shoulder or neck strap so that a user can carry it in front of the stomach or chest. This version has the advantage that the user has both hands free. Portability makes the deposition aid more flexible to use; it is particularly then no longer limited to one location.

Together with the design of the deposition aid as a portable device, particularly a handheld one, a docking station can be provided, which is preferably stationary and has a holder for the deposition aid. The user can then place the portable deposition aid, carried on the body or in the hand, into the holder and is free to carry on with different work where the deposition aid is not required.

BRIEF DESCRIPTION OF THE DRAWINGS

In the following, the invention is described by examples of embodiments in conjunction with the attached drawings. The drawings depict the invention as follows.

DETAILED DESCRIPTION

Figure 1:
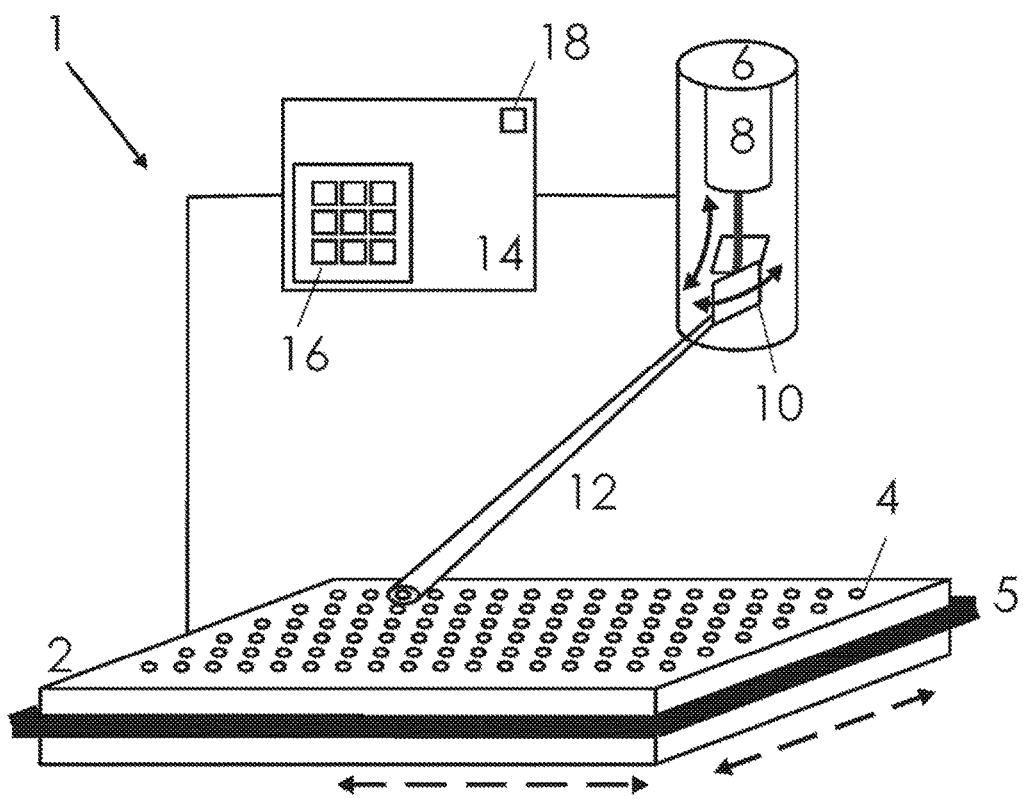
FIG. 1 is a schematic perspective view of a deposition aid according to the invention, which highlights a sample site with the help of a light effect.

FIG. 1 shows an embodiment of a deposition aid 1. A sample support 2 is arranged in a holder (black), which in this embodiment takes the form of a frame 5. A frame 5, which fixes the sample support 2 at the narrow sides, has the advantage that both the surface and the bottom of the sample support 2 are accessible to the measuring and analytical instruments. This facilitates the handling of the deposition aid, particularly if it is portable. In one version, the holder could also have the form of a well (not shown here), whose dimensions are adjusted to standardized dimensions of a sample support so that the sample support 2 can be inserted. In this example, the sample support 2 has a standardized number of six times seventeen (=102) sample sites 4. Other forms of standardized sample supports 2 with 6 to 1536 sample sites are also possible.

A device 6 with a light source 8 and guiding elements 10, here in the form of two swivel-mounted mirrors, is arranged above the surface of the sample support 2, which contains the sample sites 4. Suitable adjustment of the mirrors 10 means the light beam 12 exiting the light source 8 can be guided across the sample support 2. An adjustment is possible here using the device 6. It is of course also possible to design the sample support 2 so as to be adjustable in addition or alternatively by arranging it on an XY stage (dashed arrows), for example.

A control system 14 is provided, which communicates with the device 6 and the sample support 2. The control system 14 can detect the number, arrangement and position of the individual sample sites 4, for example, via the connection to the sample support 2, by reading out a microchip mounted on the sample support which contains the relevant configuration data, for example. As an alternative, the control system can also have a camera and a visual image recognition system (not shown here), which images the surface of the sample support and locates visible features of the sample sites for accepting the sample material. These visible features can take the form of markings, such as annular borders, on the front. Communication with the device 6 allows the control system 14 to initiate activation and deactivation of the light source 8, in this example, and to control and adjust the swivel-mounted mirrors 10.

In a semi-automatic embodiment, a user of the deposition aid 1 can enter or read in the spotting state of the sample support 2 into the control system 14 via an interface 16, for example. The user can then simultaneously specify the criteria according to which the sample sites 4 are to be selected. This can be all unspotted sample sites, for example. The control system 14 then checks which of the sample sites 4 are free for a spotting; selects one of them, on the basis of practicality, for example, and particularly so that the sample support 2 and/or the device 6 only need to be moved slightly from their current position in order to highlight the corresponding sample site 4; directs the mirrors 10 correspondingly in this example, and initiates activation of the light source 8. The light beam 12 then illuminates the selected sample site 4 and the area surrounding it on the surface of the sample support, and thus highlights it in contrast to the other not selected sample sites in a way which is visible to the human eye. The highlighting effect can be amplified by designing the sample support material so that it enhances the visual effect, for example by incorporating particles into the material of the sample support 2 which bring about a glittering or color effect when illuminated. Supported by this highlighting, the user can deposit his sample on the correct sample site 4, and then confirm, for example manually via interface 16, that spotting has taken place. This can then lead to the deactivation of the highlighting, which in this example means the light source 8 being switched off. The surface of the sample support can be provided with an antiglare coating so as to not irritate the user as he works. This can prevent glaring light reflections which could occur when the sample site is illuminated.

The control system 14 in this example also has a memory 18 for the assignment and storage of identification tags of samples and sample sites 4. If required, this information can also be entered or read in by a user via the interface 16.

Figure 2:
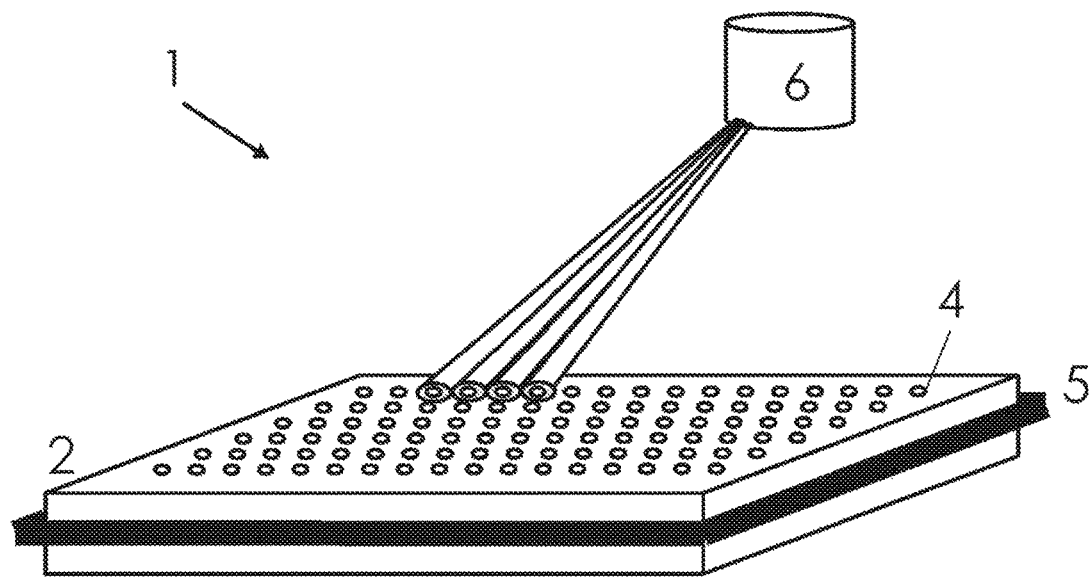
FIG. 2 is a schematic partial view of a deposition aid in a further mode of operation.

FIG. 2 depicts, in a simplified view (without control system), a sample support 2 in a frame 5 as holder, and a device 6 for highlighting several selected sample sites 4 simultaneously using a light source. This can be achieved in a continuation of the embodiment from FIG. 1 with a light beam splitter and several swivel-mounted mirrors (not shown) which can be operated independently of each other. This mode of operation can be advantageous if one type of sample from a specific sample source has to be deposited at several sample sites 4, for example to allow comparative tests with the same sample under different conditions in the mass spectrometer. The representation in FIG. 2 is intended only as an example here. The selected and highlighted sample sites 4 can also be further apart from each other and/or be distributed over the matrix of sample sites 4 on the sample support 2. Simultaneous multiple spotting of several samples is also possible.

Figure 3:
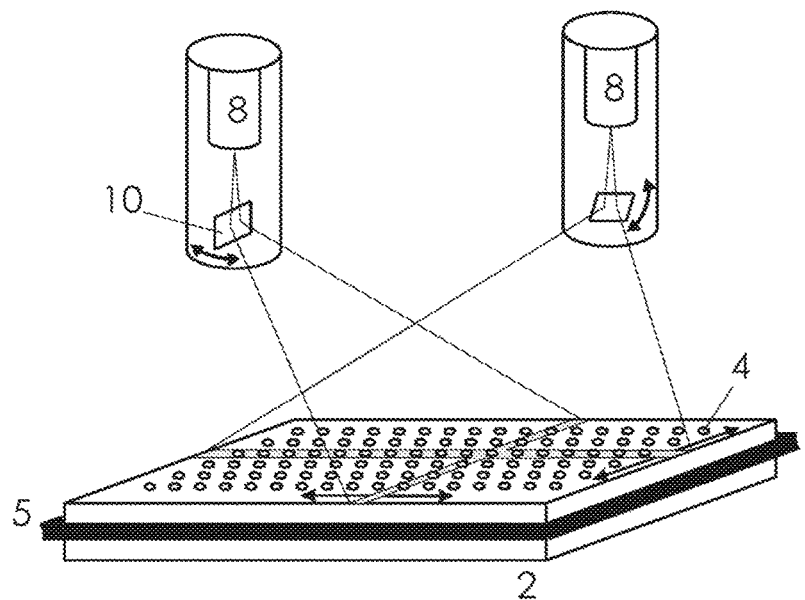
FIG. 3 is a further schematic partial view of a deposition aid which highlights a sample site with the help of a light effect.

FIG. 3 shows a further version of a deposition aid in a simplified view. This example has two light sources 8, each of which is assigned a mirror 10 as a guide element. The purpose of the light sources 8 and the guide elements 10 is to generate light bars on the front of the sample support 2, which can be adjusted—with appropriate guidance by a control system not shown here—along one direction by turning the mirrors, and which are arranged roughly perpendicular to each other. A sample site 4 can be highlighted on the sample support 2 by the point of intersection of the two light bars. This example has two light sources 8 which are arranged at a distance from each other. The light sources can also be integrated into a joint housing (not shown here) to save space. It is also possible to generate two light bars with only one light source if the light leaving the light source is split. In this case corresponding beam guides would have to be provided. The crossing light bar arrangement has in particular the advantage that shadowing of the optical highlighting during the deposition of a sample, that is, for instance, when a pipette tip or an inoculation swab approaches the sample site to be spotted and in so doing crosses the light bars, does not lead to complete obscuring of the highlighting. Instead, the outer sections of the light bars remain visible for the technician and help him to focus on the selected sample site.

Figure 4:
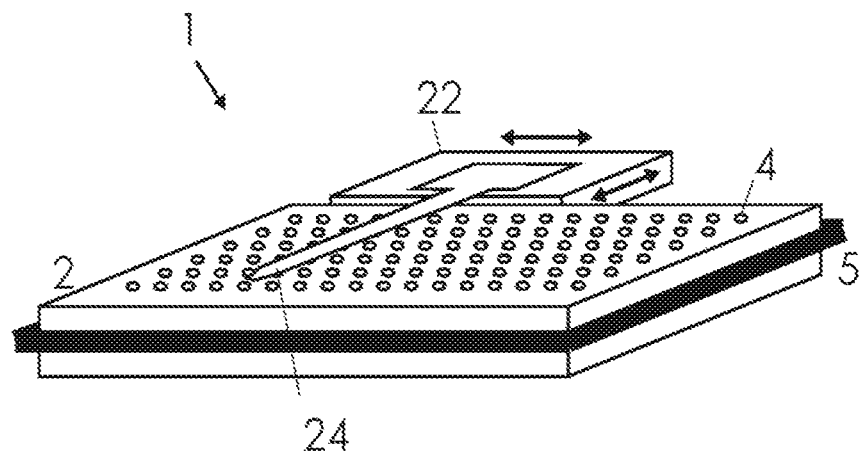
FIG. 4 is a partial schematic view of a deposition aid according to the invention which indicates a sample site mechanically by a pointer.

FIG. 4 shows a sample support 2 with sample sites 4 arranged on it and an XY translation stage 22, which is connected with an indicator 24 as the highlighting device, in this example embodiment in the form of a pointer. The control system is not shown in this representation, again for reasons of clarity. The pointer 24 has a finger with a tip, which can be directed, with the aid of the translation stage 22, toward a selected sample site 4. In the example shown, it is the fifth from the left in the front row of sample sites 4. The translation stage 22 is designed in such a way that every sample site 4 on the sample support 2 can be reached with the pointer tip. It goes without saying that, in the sense of a kinematic reversal, it is also possible to additionally or alternatively connect the sample support 2 with a translation stage. The extended finger of the pointer 24 presented in this example is also able to cover up at least some of the not selected sample sites 4 during the highlighting process, and so they cannot be incorrectly spotted.

Figure 5:
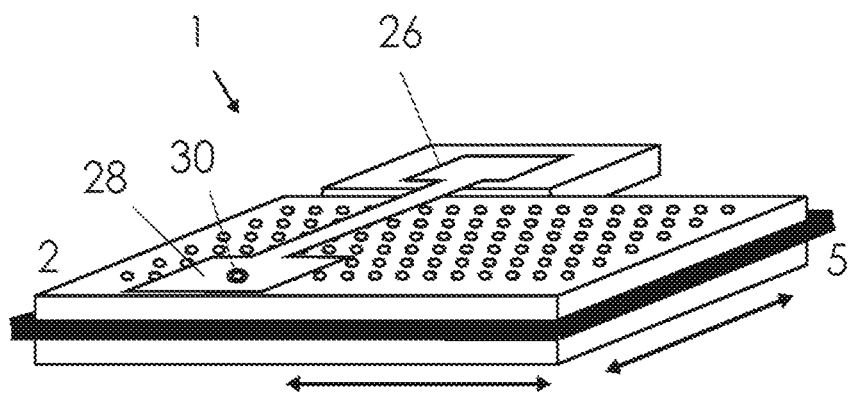
FIG. 5 is a further schematic partial view of a deposition aid according to the invention which indicates a sample site mechanically by a mask.

FIG. 5 shows a pointer as the highlighting device which has an acceptance element 26 in the form of a mask with an opening. In this example, the sample support 2 can be moved laterally in two spatial directions by a suitable movement device (an XY translation stage, for example, indicated by arrows). As in FIG. 4 the pointer comprises a finger, in this case a mask 28 with a through-opening 30 is mounted at the end of the pointer. The diameter of the through-opening 30 is large enough to allow a user to insert a sample transfer element, a stick for example (not shown), and carry out movements from side to side in order to smear a sample from the tip of the stick onto the sample site 4. The plate 28 has larger dimensions than are necessary in order to provide a frame for the through-opening 30. This serves the purpose of covering the not selected sample sites which are adjacent (on all sides) to the selected sample site 4 during the highlighting and therefore making it impossible for a user to reach them. This measure, which is additional to the highlighting, thus means that the danger of an erroneous spotting can be reduced even more.

Figure 6:
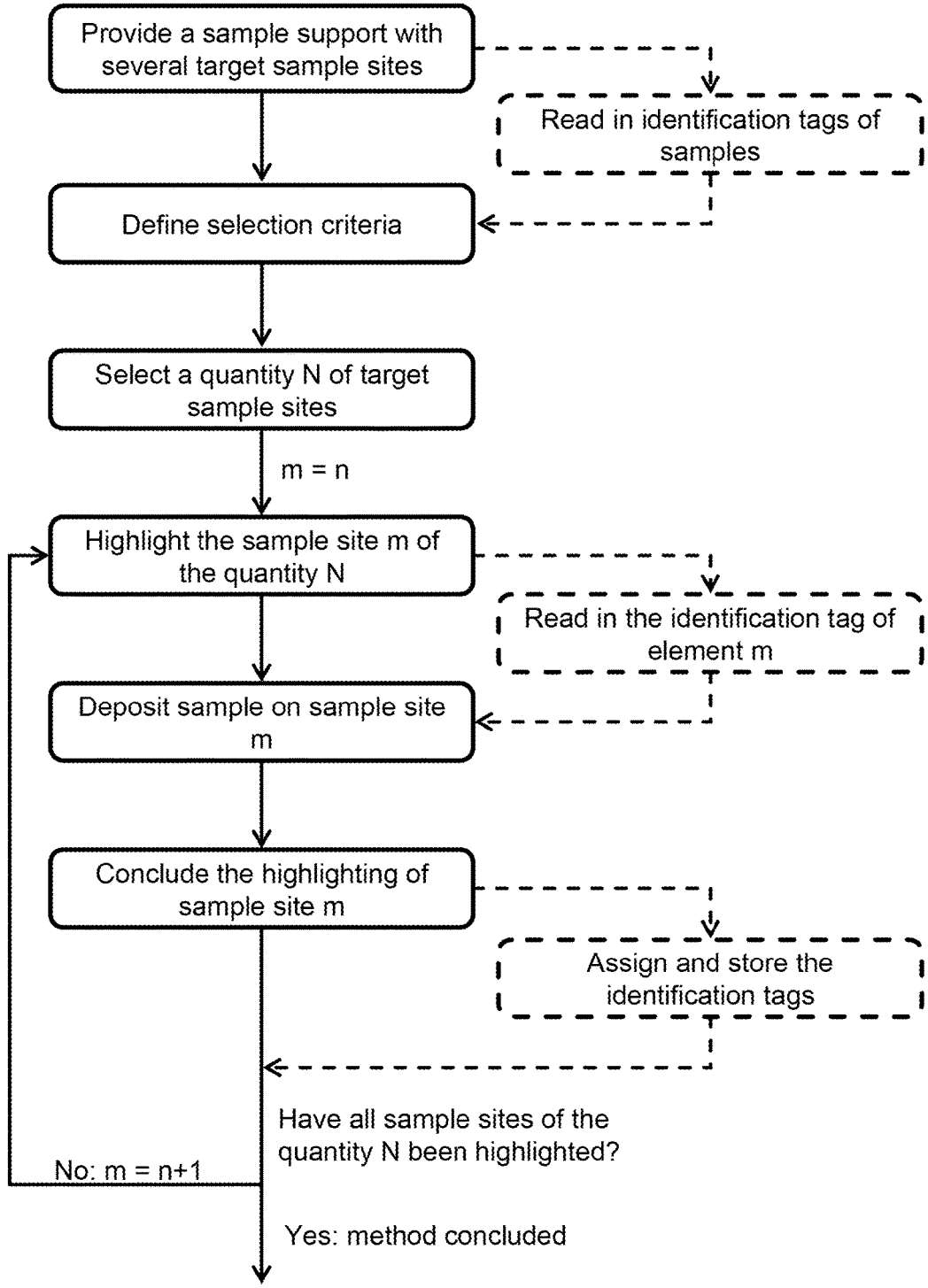
FIG. 6 is a flow chart of a method according to the invention.

FIG. 6 shows a preferred sequence of a method according to the invention as a flow chart. A sample support for ionization with matrix assisted laser desorption with several sample sites is provided. This can be a MALDI sample support, which does not need to be transparent. Moreover, a Petri dish is provided, which contains a flat nutrient medium in which colonies of microorganisms have been cultured. It is also possible that pellets obtained by means of centrifugation or filtration serve as sample sources instead of agar plates. The Petri dish mentioned here as an example can be coded with a barcode as an identification tag, which is read in as an optional method step, for example by optical scanning. Additionally or alternatively, an RFID chip could be used to hold the identification tag, which could be read out by wireless communication. The arrangement of the colonies on the nutrient medium can be photographed with a camera and evaluated with respect to the exact positioning of the individual colonies, for example with respect to the XY coordinates of the individual colonies on the flat nutrient medium. With this information, the identification tag of the nutrient medium carrier, particularly of the Petri dish, can be supplemented per sample or colony and thus specified in more detail.

Next, a selection criterion—or several selection criteria— can be defined according to which the spotting sequence is to be carried out. Possible criteria for the selection are, for example: a selection according to the numbering (for example spotting of every $n^{th}$ [unspotted] sample site), random selection, or selection using an exclusion list with already prepared sample sites. The sequence in which the sample sites which fulfill the criteria, and are therefore selected, are spotted can, in principle, be specified at will; for example it can follow a sequential numbering of the possible sample sites on the sample support from smaller numbers to larger numbers.

The first sample site selected—in one version also several sample sites—is now highlighted and manually spotted by a technician. As an option, an identification tag of the highlighted sample site can be read in between these steps in order to allow a subsequent assignment to the sample origin site. At the conclusion of the deposition process, the highlighting can be finished. In the case of a light source, this can be switched off, for example. As an option, the identification tags can then be assigned to each other and stored in a suitable storage medium, in particular in an electronic memory. If more than one sample site fulfills the selection criteria, it is possible to now iteratively process all other selected sample sites until none of the selected sample sites remains. Of course, a further, not explicitly represented criterion for the termination of the iteration is fulfilled if there are no more samples to be transferred to the sample support.

Figure 7:
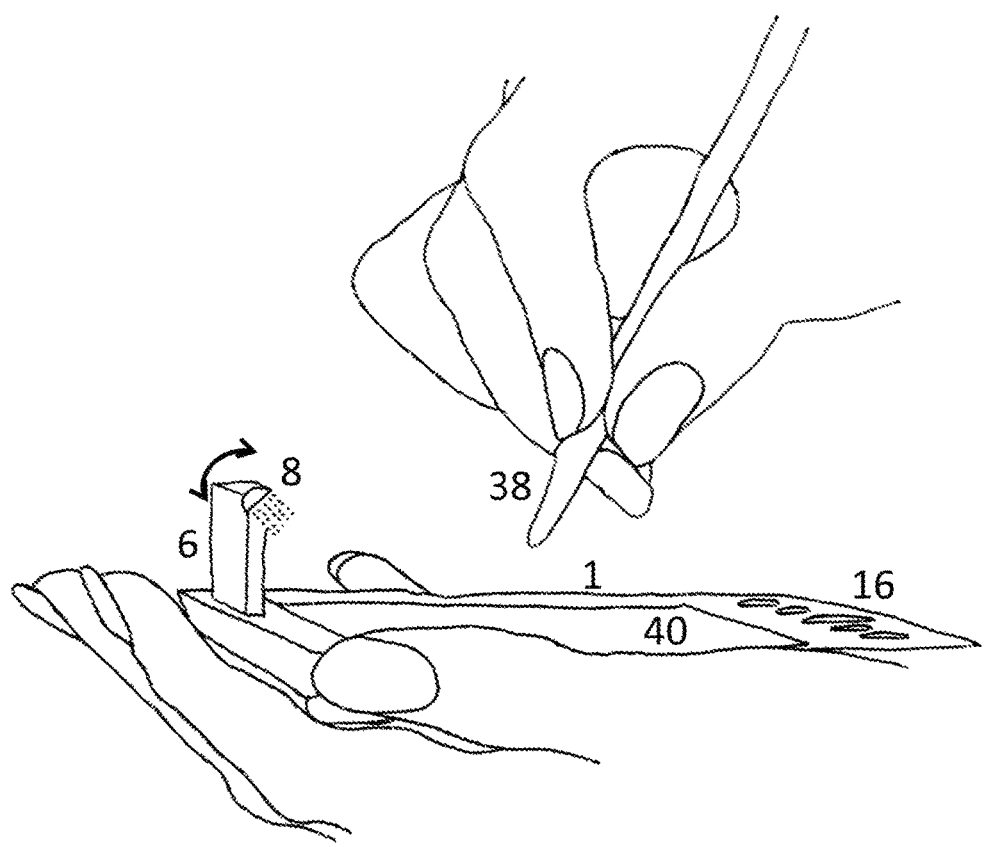
FIG. 7 is a perspective view of a deposition aid according to the invention in a portable handheld embodiment.

FIG. 7 depicts a deposition aid 1 with a holder 40 for a sample support which is not shown. The holder 40 is formed as a housing. The device for the highlighting 6 has a swivel-mounted spotlight 8 as the light source, with which every sample site on a sample support can be illuminated if the sample support is in the holder 40. In this example, the spot light 8 is mounted on an arm on the housing. The power for the spot light 8 can be supplied by an integrated battery or rechargeable battery. With a stick 38, on whose tip there is biological material of microbial origin from a colony in a Petri dish, for example, a sample can be deposited onto a sample site of the sample support positioned in the holder 40. The user of the portable deposition aid 1 can input or output data via an interface 16; it is thus possible to confirm a deposition has been carried out, for example.

The invention claimed is:

1. A deposition aid for the manual deposition of samples on a sample support for ionization with matrix assisted laser desorption, comprising:
   (a) a holder for a sample support with a plurality of sample sites which is adapted to standardized sample supports for ionization with laser desorption;
   (b) a highlighting device being located, when a sample support is inserted in the holder, substantially at an upper side of the sample support, and being configured to highlight at least one selected sample site from above, wherein light exiting from one or more light sources, using respectively associated swivel-mounted guiding elements, or light from a swivel-mounted spotlight, is guided across the sample support to the at least one selected sample site to render it visible to the human eye; and
   (c) a control system being configured to select the at least one sample site to be highlighted by the highlighting device and to control the highlighting device to highlight the at least one selected sample site from above.

2. The deposition aid according to claim 1, wherein at the at least one selected sample site, the highlighting device generates a contrast in brightness or color at least in comparison with the neighboring not selected sample sites.

3. The deposition aid according to claim 1 wherein the highlighting device is further equipped with a movable indicator, the indicator having an opening in a mask located above the sample sites which allows manual access to a selected sample site and prevents access to at least all closest neighboring not selected sample sites.

4. The deposition aid according to claim 1 further comprising a movement device which communicates with the control system and is controlled by it in such a way that it moves the holder for the sample support and the highlighting device relative to each other.

5. The deposition aid according to claim 1 wherein the control system has an interface for at least one of data input and data output.

6. The deposition aid according to claim 1 wherein the control system has a memory for the assignment and acquisition of identification tags of samples and sample sites.

7. The deposition aid according claim 1 wherein the holder comprises adapter pieces for accommodating standardized sample supports for ionization by laser desorption.

8. The deposition aid according to claim 1 wherein the highlighting device comprises a light source configured to illuminate the at least one selected sample site from above, light from the light source having an angle of incidence smaller than 30° relative to a surface of the sample support.

9. The deposition aid according to claim 5, wherein the interface has a telecommunication function.

10. The deposition aid according to claim 9, wherein the telecommunication function is established using one of wireless, BLUETOOTH® and infrared.

11. The deposition aid according to claim 1, further comprising one of a grip, blind holes suitable for a human hand, and a holding strap with which the deposition aid can be fastened to a user's arm.

12. The deposition aid according to claim 1, wherein the guiding elements comprise mirrors.

13. The deposition aid according to claim 1, wherein the highlighting device further comprises a light beam splitter so as to highlight several selected sample sites simultaneously using a light source.

14. The deposition aid according to claim 1, wherein the one or more light sources generate two light bars crossing one another on the sample support, wherein a point of intersection of the light bars highlights the at least one selected sample site.

* * * * *